US012727747B2

(12) United States Patent
Cummings

(10) Patent No.: US 12,727,747 B2
(45) Date of Patent: Sep. 8, 2026

(54) SUCTION VALVE WITH OUTWARDLY BIASED SHAFT FOR AN ENDOSCOPE

(71) Applicant: Boston Scientific Scimed, Inc., Maple Grove, MN (US)

(72) Inventor: Nathan Thomas Cummings, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 167 days.

(21) Appl. No.: 18/665,127

(22) Filed: May 15, 2024

(65) Prior Publication Data

US 2024/0382077 A1 Nov. 21, 2024

Related U.S. Application Data

(60) Provisional application No. 63/502,326, filed on May 15, 2023.

(51) Int. Cl.
*A61B 1/015* (2006.01)
*A61B 1/00* (2006.01)

(52) U.S. Cl.
CPC .......... *A61B 1/015* (2013.01); *A61B 1/00068* (2013.01)

(58) Field of Classification Search
None
See application file for complete search history.

(56) References Cited

U.S. PATENT DOCUMENTS 11,166,803 B2 * 11/2021 McGowan .............. A61F 2/013
11,213,187 B2 * 1/2022 Ono ................... A61B 1/00071
12,089,872 B2 * 9/2024 Dang ................. A61B 17/3423
2003/0069476 A1 * 4/2003 Deslauriers .............. A61B 1/32 600/207
2010/0241155 A1 * 9/2010 Chang ............... A61M 25/0662 606/196
2013/0144328 A1 * 6/2013 Weber ............... A61M 25/0074 606/200
2017/0197073 A1 7/2017 Rogier
2017/0347860 A1 12/2017 Still et al.
2018/0289460 A1 * 10/2018 McGowan ............ A61F 2/0103
2018/0326186 A1 * 11/2018 Zhou ................. A61M 25/0045
2020/0352415 A1 * 11/2020 Harris ................ A61B 1/00068
2021/0030261 A1 * 2/2021 Kress .................... A61B 1/0125
2021/0298572 A1 * 9/2021 Comee ............... A61B 1/00068
2022/0151463 A1 * 5/2022 Fancher ............... A61B 1/0052
2022/0221069 A1 * 7/2022 Ng ..................... A61B 1/00068
2022/0361734 A1 * 11/2022 Ko ..................... A61B 1/00068
2022/0395626 A1 * 12/2022 Kallenberger ......... A61B 34/30
2024/0165354 A1 * 5/2024 Ishikita ............. A61M 16/0463

FOREIGN PATENT DOCUMENTS

CN 1107216 A 8/1995

OTHER PUBLICATIONS

International Search Report and Written Opinion for International Application No. PCT/US2021/029452, dated Sep. 19, 2024. (10 Pages).

* cited by examiner

*Primary Examiner* — Mohammad J Rahman
(74) *Attorney, Agent, or Firm* — Seager, Tufte & Wickhem, LLP

(57) ABSTRACT

Devices, systems, and methods for a suction valve assembly for a medical device. The suction valve assembly includes a valve member with a valve shaft that slides within a valve well. The valve shaft includes one or more slits and is biased to expand outward and press against internal walls of the valve well.

20 Claims, 10 Drawing Sheets

SUCTION VALVE WITH OUTWARDLY BIASED SHAFT FOR AN ENDOSCOPE

CROSS-REFERENCE TO RELATED APPLICATIONS

This application claims the benefit of U.S. Provisional Patent Application Ser. No. 63/502,326 filed on May 15, 2023, the disclosure of which is incorporated herein by reference.

TECHNICAL FIELD

This disclosure relates generally to valve assemblies and methods, and particularly to suction valve assemblies and methods for an endoscope.

BACKGROUND

A wide variety of intracorporeal medical devices and systems have been developed for medical use, for example, for endoscopic procedures. Some of these devices and systems include guidewires, catheters, catheter systems, endoscopic instruments, and the like. These devices and systems are manufactured by any one of a variety of different manufacturing methods and may be used according to any one of a variety of methods. Of the known medical devices, systems, and methods, each has certain advantages and disadvantages. There is an ongoing need to provide alternative medical devices and systems as well as alternative methods for manufacturing and using medical devices and systems.

SUMMARY

This disclosure provides design, material, manufacturing method, and use alternatives for medical devices and medical systems. In a first example, a suction valve assembly for a medical device can comprise a valve body having a cylindrical valve well with internal walls, an inlet channel in fluid communication with the valve well, and an outlet channel in fluid communication with the valve well; and a valve member having a valve shaft, the valve shaft having an inlet opening and positioned within the valve well to slide along the internal walls between a closed position where the inlet opening abuts a portion of the internal walls and an open position where the inlet opening is aligned with the inlet channel of the valve body. The valve shaft can have one or more slits extending through a side surface of the shaft allowing the valve shaft to expand outwards, the valve shaft biased to expand outwards to a diameter greater than an inner diameter defined by the internal walls of the cylindrical valve well.

Alternatively or additionally to any of the examples above, the valve member can include a cap accessible from outside the valve body, the cap in mechanical communication with the valve shaft such that actuating the cap slides the valve shaft into the open position.

Alternatively or additionally to any of the examples above, the valve member can include a neck connecting the valve cap to the valve shaft.

Alternatively or additionally to any of the examples above, the neck can include a flat portion and a rounded portion shaped to resist rotation of the valve member within the valve body.

Alternatively or additionally to any of the examples above, the valve well can extend the length of the longest dimension of the valve body between a top face and an opposing bottom face of the valve body.

Alternatively or additionally to any of the examples above, the inlet channel can be positioned within an internal wall of the valve well.

Alternatively or additionally to any of the examples above, the outlet channel can be positioned within the bottom face of the valve body.

Alternatively or additionally to any of the examples above, the valve shaft can have only one slit extending through a side surface of the shaft allowing the valve shaft to expand outwards.

Alternatively or additionally to any of the examples above, the valve shaft can have slits extending through side surfaces of the shaft allowing the valve shaft to expand outwards.

Alternatively or additionally to any of the examples above, the two slits can be on opposite sides of the valve shaft.

Alternatively or additionally to any of the examples above, the valve member can include a plurality of ribs across the one or more slits within the valve shaft.

Alternatively or additionally to any of the examples above, the valve member can be made of a single piece of uniform material.

Alternatively or additionally to any of the examples above, the suction valve assembly can further include a valve skirt having one or more wedge members, the valve skirt configured such that, when the valve shaft is in the closed position, each of the one or more wedge members presses against one of the one or more slits in the valve shaft to bias the valve shaft outwards towards the internal walls of the valve well.

Alternatively or additionally to any of the examples above, the valve member can be made of polycarbonate plastic.

In another example, an endoscopic surgical device comprises an endoscopic probe, a suction valve assembly according to any of the examples above, and a source of suction in fluid communication with the inlet channel of the suction valve assembly, such that opening the valve provides suction to the endoscopic probe from the inlet channel, through the valve well, and into the outlet channel. The outlet passage of the suction valve assembly is in fluid communication with the endoscopic probe.

In another example, a suction valve assembly can be for use in an endoscope having a lumen configured to extend into a patient's body cavity. The suction valve assembly comprises a valve body having a cylindrical valve well with internal walls, an inlet channel in fluid communication with the valve well, and an outlet channel in fluid communication with the valve well; and a valve member having a valve shaft, the valve shaft having an inlet opening and positioned within the valve well to slide along the internal walls between a closed position where the inlet opening abuts a portion of the internal walls and an open position where the inlet opening is aligned with the inlet channel of the valve body. The valve shaft can have one or more slits extending through a side surface of the shaft allowing the valve shaft to expand outwards, the valve shaft biased to expand outwards to a diameter greater than an inner diameter defined by the internal walls of the cylindrical valve well.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various embodiments and together with the description serve to explain the principles of the present disclosure.

Figure 1:
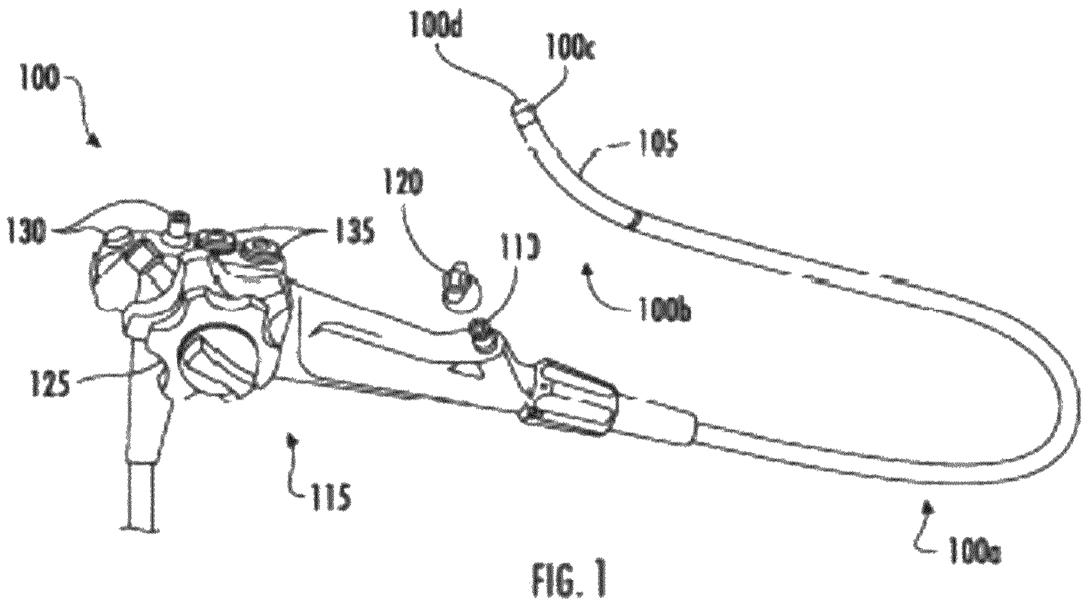
FIG. 1 depicts a schematic view of components of an illustrative endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an illustrative medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, wherein like elements are referred to with the same reference numerals.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is illustrative only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The detailed description is intended to illustrate but not limit the disclosure. Those skilled in the art will recognize that the various elements described may be arranged in various combinations and configurations without departing from the scope of the disclosure. The detailed description illustrates example embodiments of the disclosure.

Figure 2:
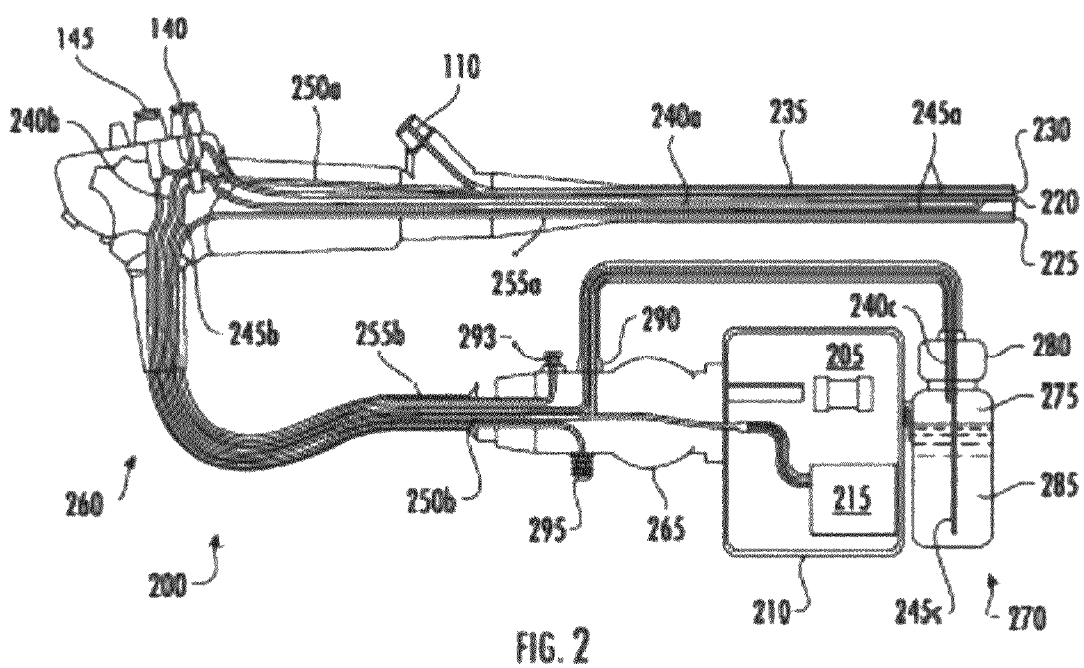
FIG. 2 depicts a schematic view of components of an illustrative endoscope system.

With reference to FIG. 1, an illustrative endoscope 100 is depicted and FIG. 2 depicts an illustrative endoscope system 200. The endoscope 100 may include an elongated tube or shaft **100*a*** that is configured to be inserted into a subject (e.g., a patient).

A light source 205 of the endoscope system 200 may feed illumination light to a distal portion **100*b* of the endoscope 100. The distal portion 100*b* of the endoscope 100 may house an imager (e.g., CCD or CMOS imager) (not shown). The light source 205 (e.g., lamp) may be located in a video processing unit 210 that processes signals input from the imager and outputs processed video signals to a video monitor (not shown) for viewing. The video processing unit 210 may also serve as a component of an air/water feed circuit by housing a pressurizing pump 215, such as an air feed pump, in the unit 210**.

The endoscope shaft **100*a* may include a distal tip 100*c* (e.g., a distal tip unit) provided at the distal portion 100*b* of the shaft 100*a* and a flexible bending portion 105 proximal to the distal tip 100*c*. The flexible bending portion 105 may include an articulation joint (not shown) to assist with steering the distal tip 100*c*. On an end face 100*d* of the distal tip 100*c* of the endoscope 100 is a gas/lens wash nozzle 220 for supplying gas to insufflate the interior of the patient at the treatment area and for supplying water to wash a lens covering the imager. An irrigation opening 225 in the end face 100*d* supplies irrigation fluid to the treatment area of the patient. Illumination windows (not shown) that convey illumination light to the treatment area, and an opening 230 to a working channel 235 extending along the shaft 100*a* for passing tools to the treatment area, may also be included on the face 100*d* of the distal tip 100*c*. The working channel 235 may extend along the shaft 100*a* to a proximal channel opening 110 positioned distal to an operating handle 115 (e.g., a proximal handle) of the endoscope 100. A biopsy valve 120 may be utilized to seal the channel opening 110** against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115.

The handle 115 may be provided with dual valve locations 135. One of the valve locations 135 may receive a gas/water valve 140 for operating an insufflating gas and lens water feed operation. A gas supply line **240*a* and a lens wash supply line 245*a* run distally from the gas/water valve 140 along the shaft 100*a* and converge at the distal tip 100*c* proximal to the gas/wash nozzle 220 (FIG. 2**).

The other valve location 135 may receive a suction valve 145 for operating a suction operation. A suction supply line **250*a* may run distally from the suction valve 145 along the shaft 100*a* to a junction point in fluid communication with the working channel 235 of the endoscope 100**.

The operating handle 115 may be electrically and fluidly connected to the video processing unit 210, via a flexible umbilical 260 and connector portion 265 extending therebetween. The flexible umbilical 260 has a gas (e.g., air or CO2) feed line **240*b*, a lens wash feed line 245*b*, a suction feed line 250*b*, an irrigation feed line 255*b*, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100*a* to transmit light to the distal tip 100*c* of the endoscope 100. The connector portion 265 when plugged into the video processing unit 210 also connects the air pump 215 to the gas feed line 240*b* in the umbilical 260**.

A water reservoir or container 270 (e.g., water bottle) may be fluidly connected to the endoscope 100 through the connector portion 265 and the umbilical 260. A length of gas supply tubing **240*c* passes from one end positioned in an air gap 275 between the top 280 (e.g., bottle cap) of the reservoir 270 and the remaining water 285 in the reservoir to a detachable gas/lens wash connection 290 on the outside of the connector portion 265. The gas feed line 240*b* from the umbilical 260 branches in the connector portion 265 to fluidly communicate with the gas supply tubing 240*c* at the detachable gas/lens wash connection 290, as well as the air pump 215. A length of lens wash tubing 245*c*, with one end positioned at the bottom of the reservoir 270, may pass through the top 280 of the reservoir 270 to the same detachable connection 290 as the gas supply tubing 240*c* on the connector portion 265. In other embodiments, the connections may be separate and/or separated from each other. The connector portion 265 may also have a detachable irrigation connection 293 for irrigation supply tubing (not shown) running from a source of irrigation water (not shown) to the irrigation feed line 255*b* in the umbilical 260. In some embodiments, irrigation water is supplied via a pump (e.g., peristaltic pump) from a water source independent (not shown) from the water reservoir 270. In other embodiments, the irrigation supply tubing and lens wash tubing 245*c* may source water from the same reservoir. The connector portion 265 may also include a detachable suction connection 295 for suction feed line 250*b* and suction supply line 250*a* fluidly connecting a vacuum source (e.g., hospital house suction) (not shown) to the umbilical 260 and endoscope 100**.

The gas feed line **240*b* and lens wash feed line 245*b* may be fluidly connected to the valve location 135 for the gas/water valve 140 and configured such that operation of the gas/water valve in the well controls supply of gas or lens wash to the distal tip 100*c* of the endoscope 100. The suction feed line 250*b* is fluidly connected to the valve location 135 for the suction valve 145 and configured such that operation of the suction valve 145 in the well controls suction applied to the working channel 235 of the endoscope 100**.

The suction valve 145 may be configured to allow or prevent suction and/or a suction effect in the working channel 235. When the suction valve 145 is in a valve closed position (e.g., a first configuration), a suction fluid flow through the working channel 235 may be blocked by the suction valve 145. When suction is desired in the working channel 235, an operator or user may actuate the suction valve 145 (e.g., by depressing a button on the valve and/or actuating the suction valve 145 in one or more other suitable manners) in order to bring the suction valve 145 to a valve open position (e.g., a second configuration). When the suction valve 145 is in the valve opened position, a flow channel inside the suction valve may connect the working channel 235 to the suction device coupled to suction connection 295 and the suction device may create a negative pressure that draws fluid into and out of the working channel 235 through an outlet provided in the suction valve. When the operator or user releases the suction valve 145, the valve 145 may return to its valve closed position and reduce or block a suction fluid flow from the working channel 235.

In some cases, suction valves 145 may rely on a path of least resistance to direct suction fluid flow through the endoscope system 200. In some cases, when a suction pump is turned on for a procedure, the pump remains on for an entirety of the procedure and continually pulls air from the flexible umbilical 260, which in turn draws fluid from the line side of the endoscope 100 that runs up the umbilicus 260 and connects to a port at the suction valve 145. When the suction valve 145 is in a first position and/or configuration (e.g., a closed position) the suction force or negative pressure from the suction pump is blocked from the working channel 235 and may pull fluid from atmosphere through the suction valve 145. When the suction valve 145 is actuated to a second position and/or configuration (e.g., an opened position) (e.g., when the button or cap associated with the suction valve 145 is depressed and/or actuated in one or more other suitable manners), the opening from atmosphere through the suction valve 145 to the suction pump may be effectively closed or blocked by the suction valve 145 and a fluid path between working channel 235 and the suction pump through the suction valve 145 may be opened. Thus, fluid moving to the suction pump may follow a path of least resistance, where the path may change depending on whether the suction valve 145 is in a first position (e.g., a closed position) or a second position (e.g., an opened position)

In some cases, valve stems of suction valves 145 may be configured to have a close fit with a valve well configured to receive the valve stem in the endoscope 100. In such suction valves 145, when the valve stem is in a first position the close fit blocks a flow path or increases a resistance to flow between the working channel 235 and the suction pump and reduces a resistance to flow between atmosphere and the suction pump. Similarly, when the valve stem is in a second position, the close fit blocks a flow path or increases a resistance to flow between the atmosphere and the suction pump and reduces a resistance to flow between the working channel 235 and the suction pump.

Suction valves 145 configured to block flow using close fits between the valve stem and valve well requires valves stems that are precisely manufactured. The precision required to produce suction valves with close fits requires expensive materials (e.g., metals, etc.), highly precise machinery, and is time consuming to achieve.

Additionally, suction valves 145 with close fit valve stems and valve wells are manufactured to have at least some clearance to allow the valve stem to adjust positions within the valve well. This clearance, may result in leakage during use, which may lead to two issues noticeable by a physician. The first is when the suction valve 145 is in a position intended to block suction from the working channel 235, there is still some suction flow passing through the working channel 235 and the suction valve 145 to the suction pump. The smaller the clearance between the valve stem and the valve well, the less unwanted flow through the working channel 235 that occurs and the larger the clearance, the more unwanted flow through the working channel 235, however, clearance is needed to facilitate movement of the valve stem within the valve well. When flow is actively moving up the working channel 235 in such configurations of the suction valve 235, users may perceive the suction as "poor insufflation" due to the suction of the suction pump pulling volume from a body lumen in which the user is working, even when the suction valve 145 is in a position intended to block a suction flow from the working channel 235. Second, when a valve stem of the suction valve 145 is in a position within a valve well to facilitate a suction flow between the working channel 235 and the suction pump through the suction valve 145, the flow from atmosphere to the suction pump may not be completely blocked. Any such leaking from atmosphere may reduce a pressure differential between suction valve and the distal end of the working channel 235, which leads to a reduced suction force or negative pressure, reduced flow rates, and aerated flow through the fluid path to the suction pump.

Suction valves 145 configured to operate with close-fit valve stems and valve wells may work well enough when intended for re-use in multiple procedures, as a price point for such suction valves can be high enough to justify manufacturing the suction valves 145 from materials and with the necessary precision that can achieve and maintain desired tolerances over the life of the reusable suction valves 145. However, a price point of a single use suction valve may not allow for use of the necessary materials, tools, and/or precise manufacturing required to achieve and/or maintain tolerances over the life of single-use suction valves.

Figure 3A:
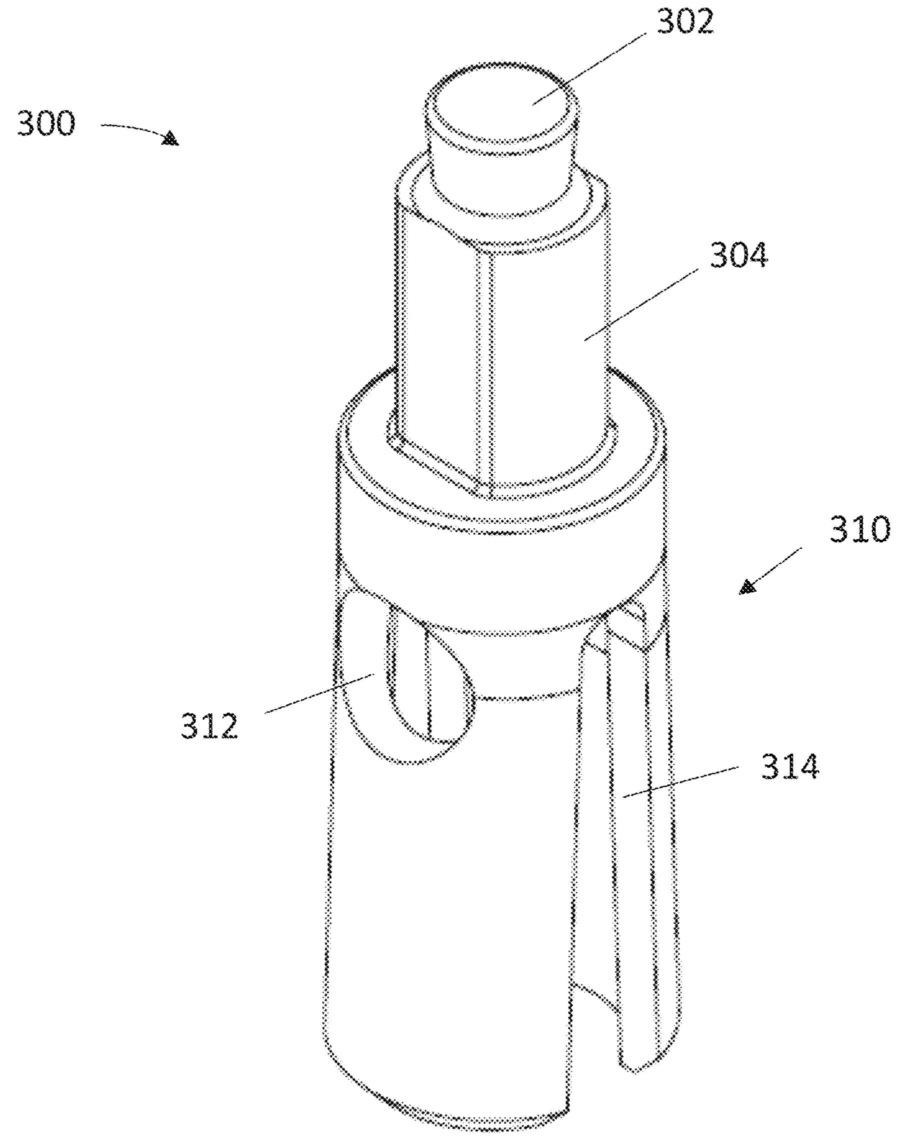
FIG. 3A depicts a schematic perspective view of an illustrative suction valve member.

The suction valve configurations for endoscopes 100 and/or other suitable scopes discussed herein address the above-noted concerns with existing suction valves and are configured to mitigate and/or eliminate leakage along an unintended flow path through the suction valve 145. FIG. 3A depicts a schematic perspective view of an illustrative suction valve member 300 configured to address these concerns.

As shown in FIG. 3A, the suction valve member 300 includes a cap 302, a valve neck 304, and a valve shaft 310. The valve shaft 310 further includes inlet openings 312 and shaft slits 314. In this embodiment of the member 300, the shaft 300 includes two symmetrical slits 314 located radially opposite each other along the shaft sidewalls.

Although the valve neck may have a fully circular cross-section in alternative embodiments, FIG. 3A shows the valve neck 304 with alternating flat and curved surfaces that correspond to the shape of an opening in the valve body. This prevents the valve member 300 from rotating relative to the valve body and assures that the proper passages will be aligned when the valve is open and obstructed when the valve is closed.

Figure 3B:
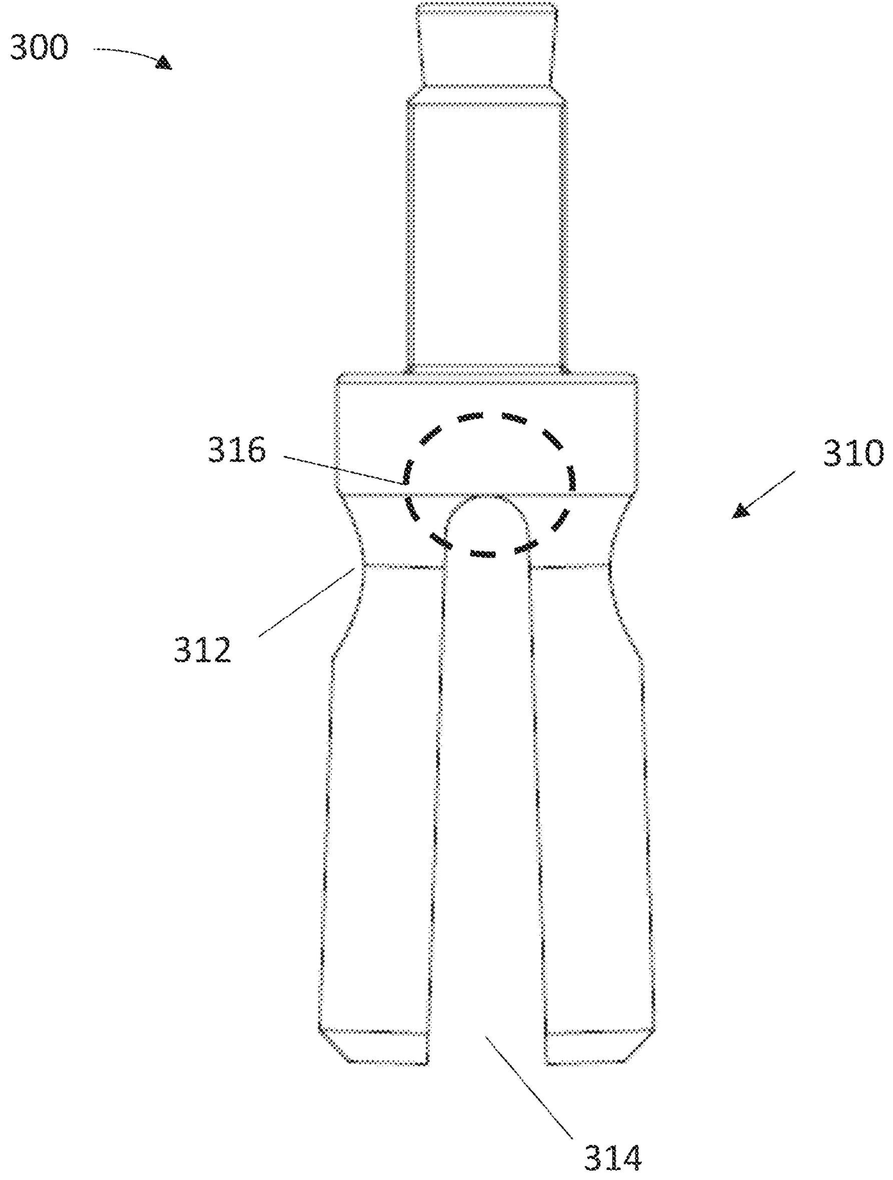
FIG. 3B depicts a side view of the illustrative suction valve member of FIG. 3A.

In the side view of the member 300 shown in FIG. 3B, it can be seen that the side walls of the shaft 310 flare at an outward angle when not constrained. This angle may be, for example, less than 5 degrees, and may be the natural result of the valve's manufacture as further described herein. A region of deformation 316, at the top of each slit 314 within the shaft 310, may contract to allow movement of the lower part of the shaft 310 between the flared angle shown in FIG. 3B and a substantially parallel angle as shown in FIGS. 3C and 3D.

Figure 3C:
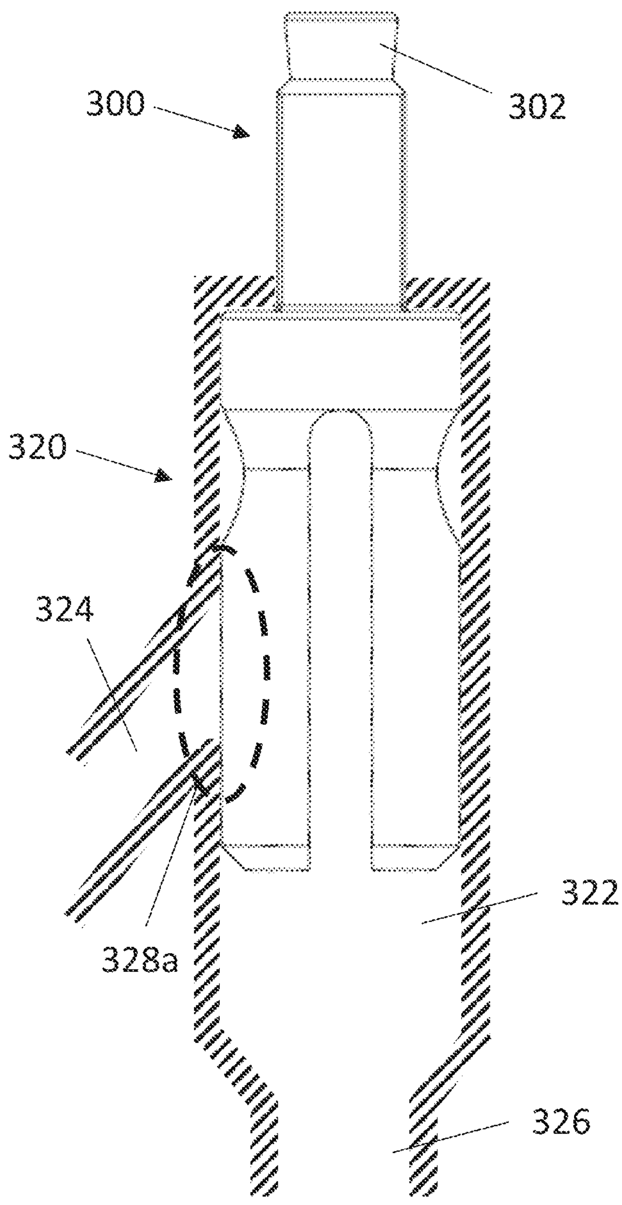
FIG. 3C depicts a side view of a suction valve assembly including the illustrative suction valve member of FIGS. 3A and 3B, with the suction valve assembly in a first configuration.
Figure 3D:
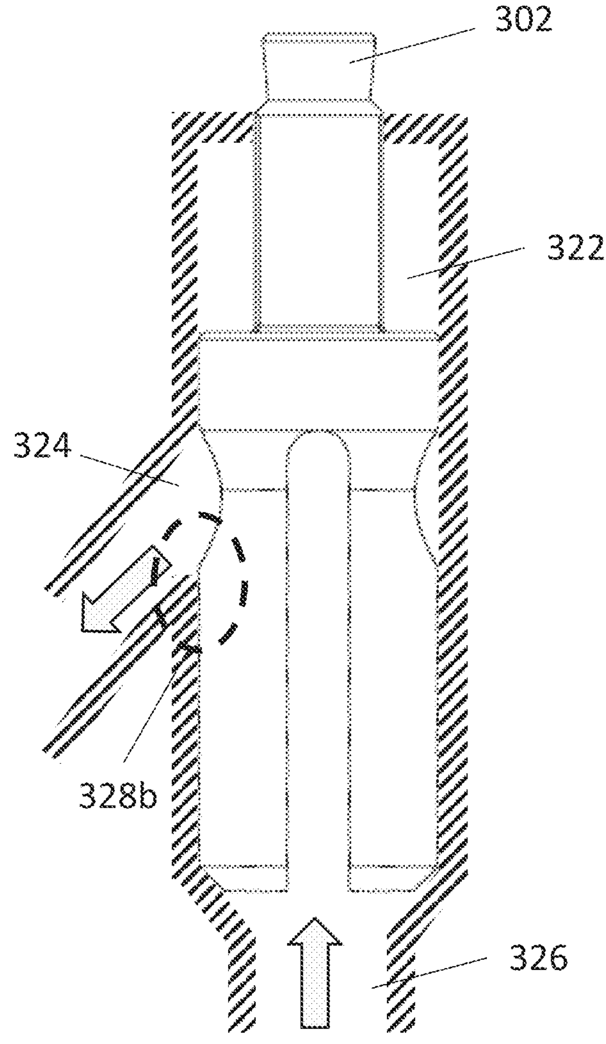
FIG. 3D depicts a side view of the suction valve assembly of FIG. 3C, with the suction valve assembly in a second configuration.

FIGS. 3C and 3D show the valve member 300 interacting with a valve body 320 in accordance with embodiments of the disclosure. The valve body 320 includes a valve well 322, an inlet passage 324, and an outlet passage 326. In FIG.

3C, the side wall of the valve shaft 310 blocks the inlet passage 324; the valve is closed.

When a user presses on the cap 302, the valve member 300 slides downward within the valve well 322 until the inlet opening 312 aligns with the passage 324, opening the valve as shown in FIG. 3D. The passage 324 is in fluid communication with a source of suction, resulting in fluid flow in the directions shown in the arrows.

Due to the outward bias in the valve shaft 310, the shaft presses against the valve well 322 in both the open and closed positions. In the closed position, this force helps maintain a seal between the side wall of the shaft 310 and the inlet passage 324, at the region 328*a* shown by the dotted circle in FIG. 3C.

The outward bias in the valve shaft 310 also acts to seal the air channel when the valve is open. The shaft 310 presses against the wall below the passage 324 at the region 328*b* shown by the dotted circle in FIG. 3D.

Figures 4, 5:
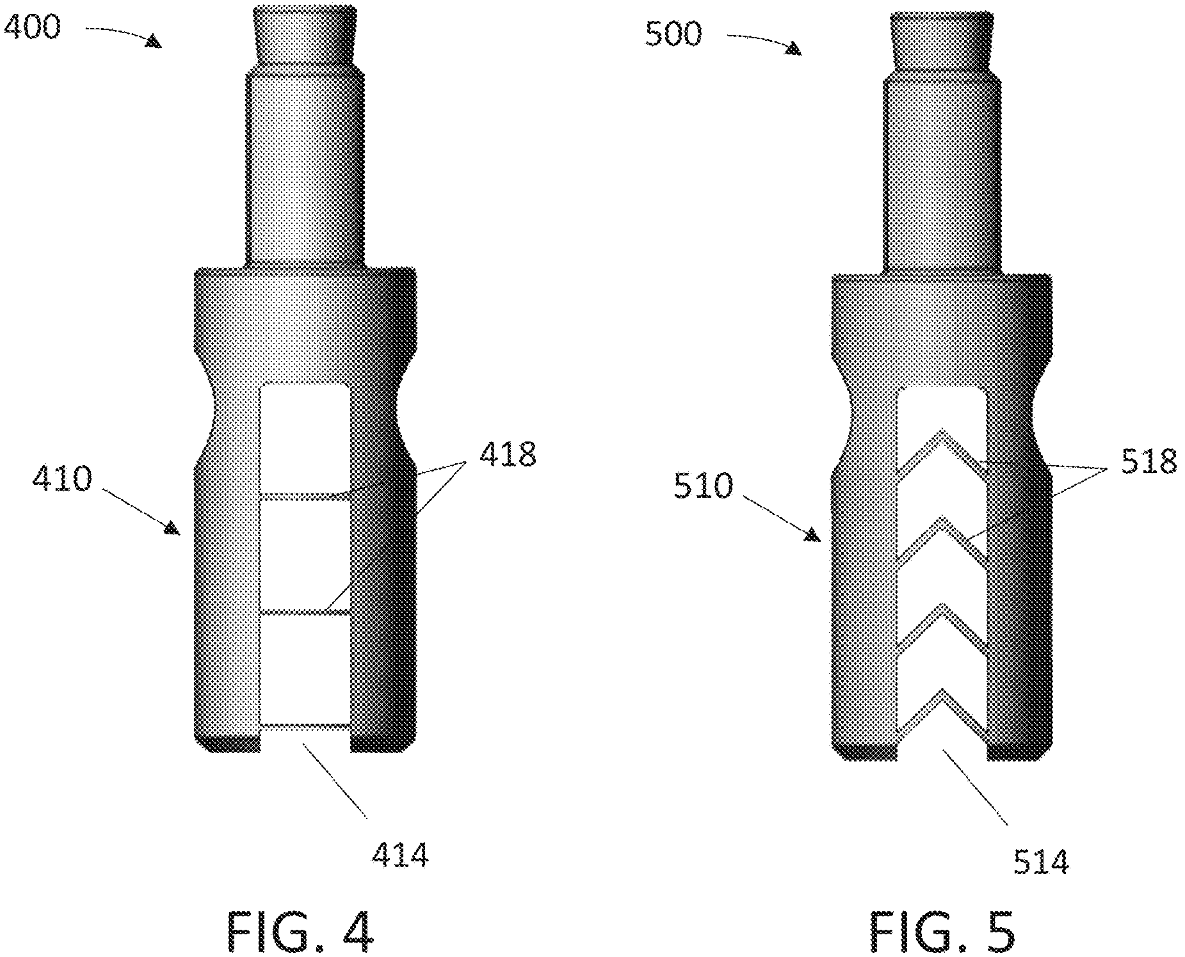
FIG. 4 depicts a schematic side view of an illustrative suction valve member.
FIG. 5 depicts a schematic side view of an illustrative suction valve member.

Other designs for the valve member are possible, such as those shown in FIGS. 4 and 5. Valve member 400 has a shaft 410 with slits 414, but with the addition of ribs 418. The ribs 418 provide additional strength to the shaft 410 and resist inward deformation of the shaft walls. Similarly, the shaft 510 of the valve member 500 includes ribs 518 within the slits 514, which, due to an intermediate angle in each rib 518, may be more yielding than the ribs 418 while still providing some additional support.

Figures 6A, 6B, 6C:
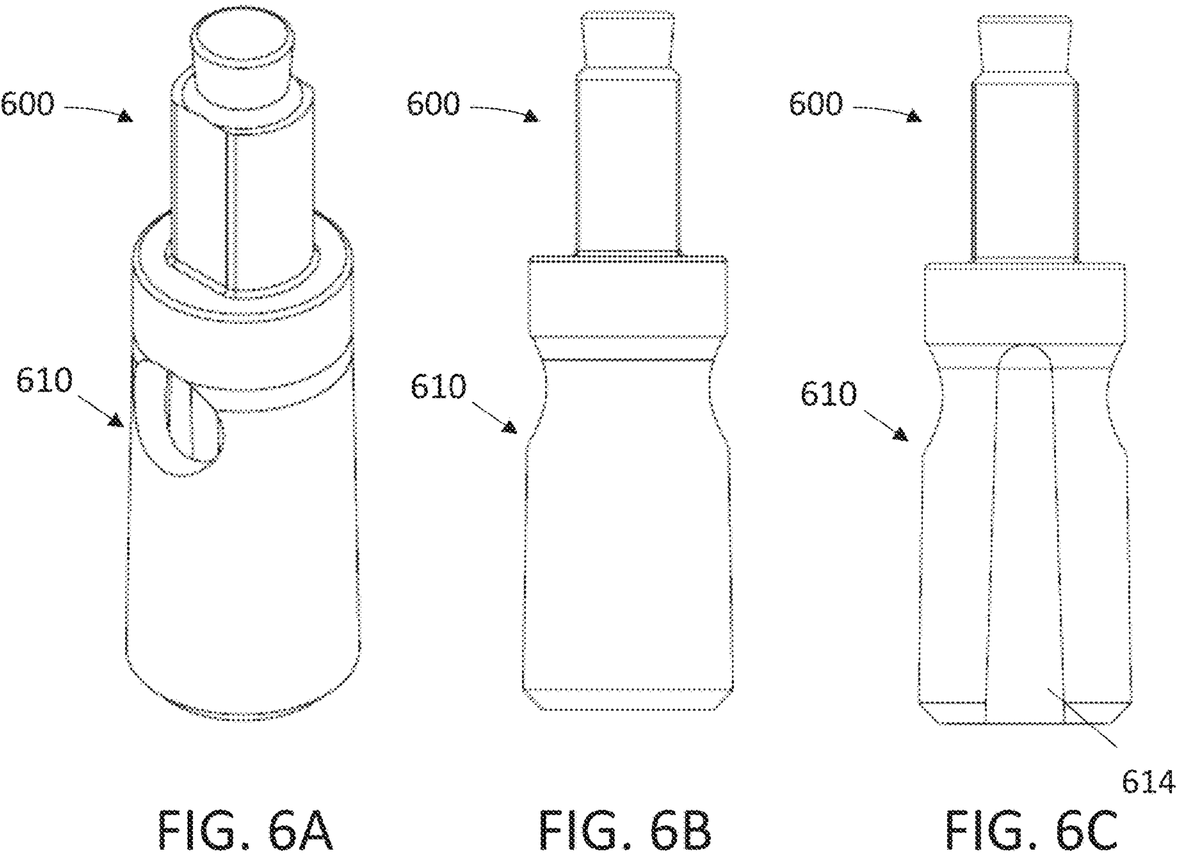
FIG. 6A depicts a schematic perspective view of an illustrative suction valve member.
FIG. 6B depicts a first side view of the illustrative suction valve member of FIG. 3A.
FIG. 6C depicts an opposite side view of the illustrative suction valve member of FIG. 6A.

FIGS. 6A-6C illustrate another embodiment of a valve member 600 in which the valve shaft 610 has one slit 614 rather than two slits. Depending on how much deformation is necessary for a particular valve configuration, any of the two-slit designs described herein could potentially be made with only one slit. In some implementations, the slit may be sized or shaped differently to accommodate the lack of a corresponding slit on the opposite side. Furthermore, while the slits herein have been shown orthogonal to the inlet openings (that is, disposed 90 degrees around the shaft wall relative to the inlet openings), it will be understood that the slits could in fact be located at other relative locations if asymmetric deformation of the shaft is preferred.

FIGS. 7A-7D illustrate an embodiment of a suction valve containing both a valve member 700 and valve skirt 730. The valve skirt 730 includes a neck opening 732 sized and shaped to accommodate the valve neck 704.

The valve member 700 includes tapered slits 714 that are opened at the top of the valve shaft 710. Wedges 734 protruding from the underside of the valve skirt 730 fit within the tapered slits 714 when the valve is in the closed position, pushing the sides of the valve shaft 710 outward.

Figures 7A, 7B:
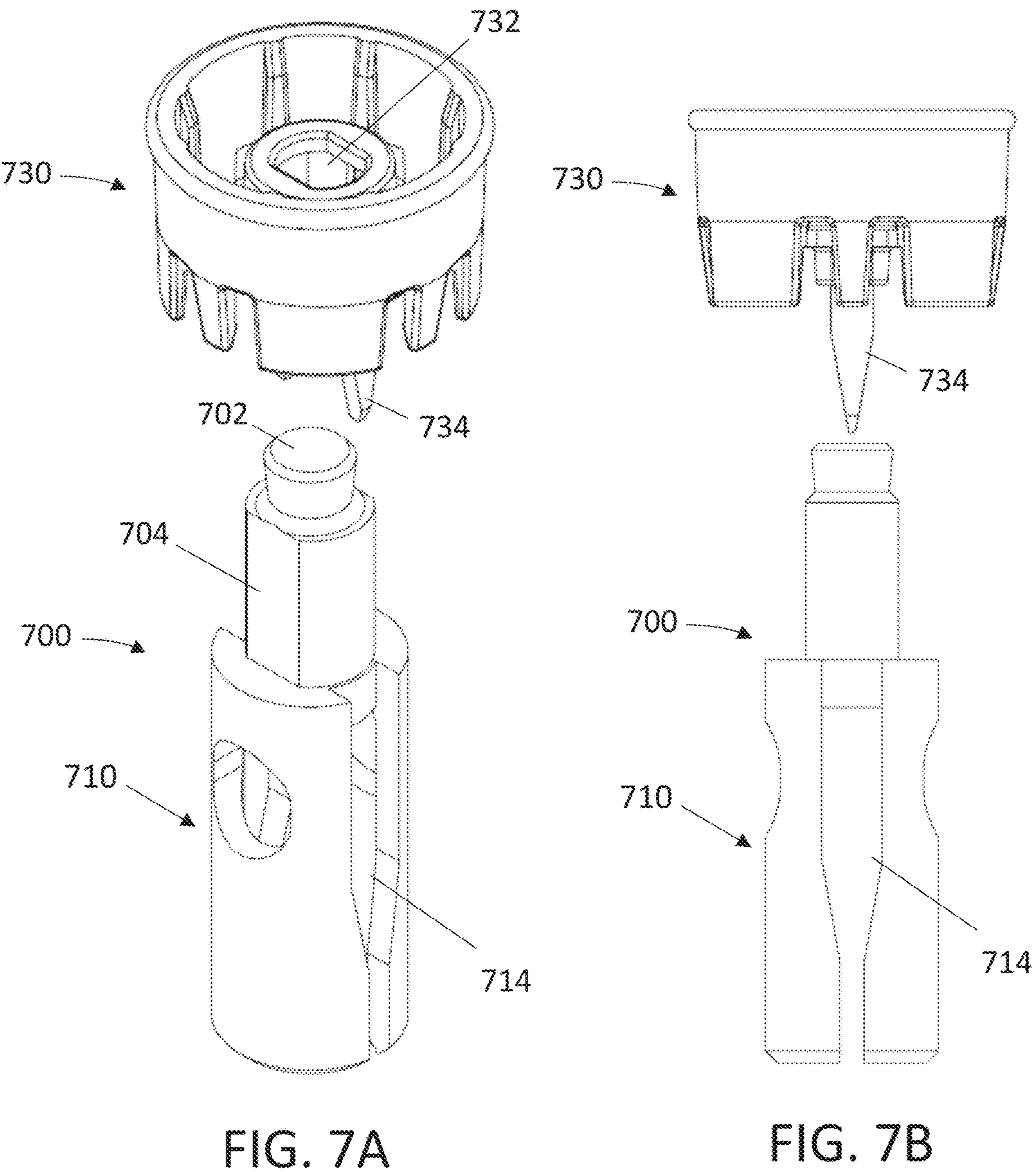
FIG. 7A depicts an exploded schematic perspective view of an illustrative suction valve member and valve skirt.
FIG. 7B depicts an exploded side view of the illustrative suction valve member and valve skirt of FIG. 7A.
Figure 7C:
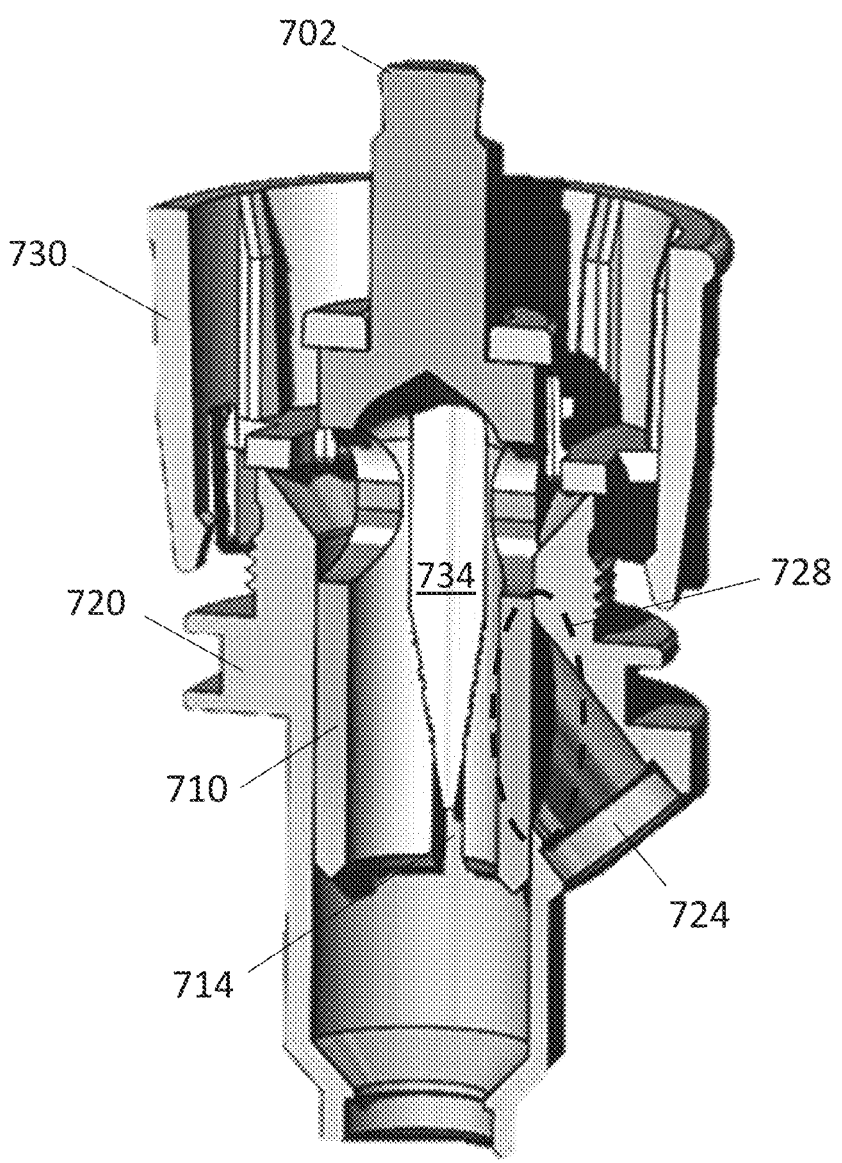
FIG. 7C depicts a cross-section view of an illustrative suction valve assembly, including the suction valve member and valve skirt of FIGS. 7A and 7B, in a closed position.

The valve skirt 730 and one or more wedges 734 remain stationary with the valve body 720. When the valve member 700 is positioned to close the valve, as shown in FIG. 7C, the one or more wedges 734 push outward on the valve shaft 710, which causes the shaft walls to push against the inlet passage 724, creating a seal against suction in the circled region 728.

Figure 7D:
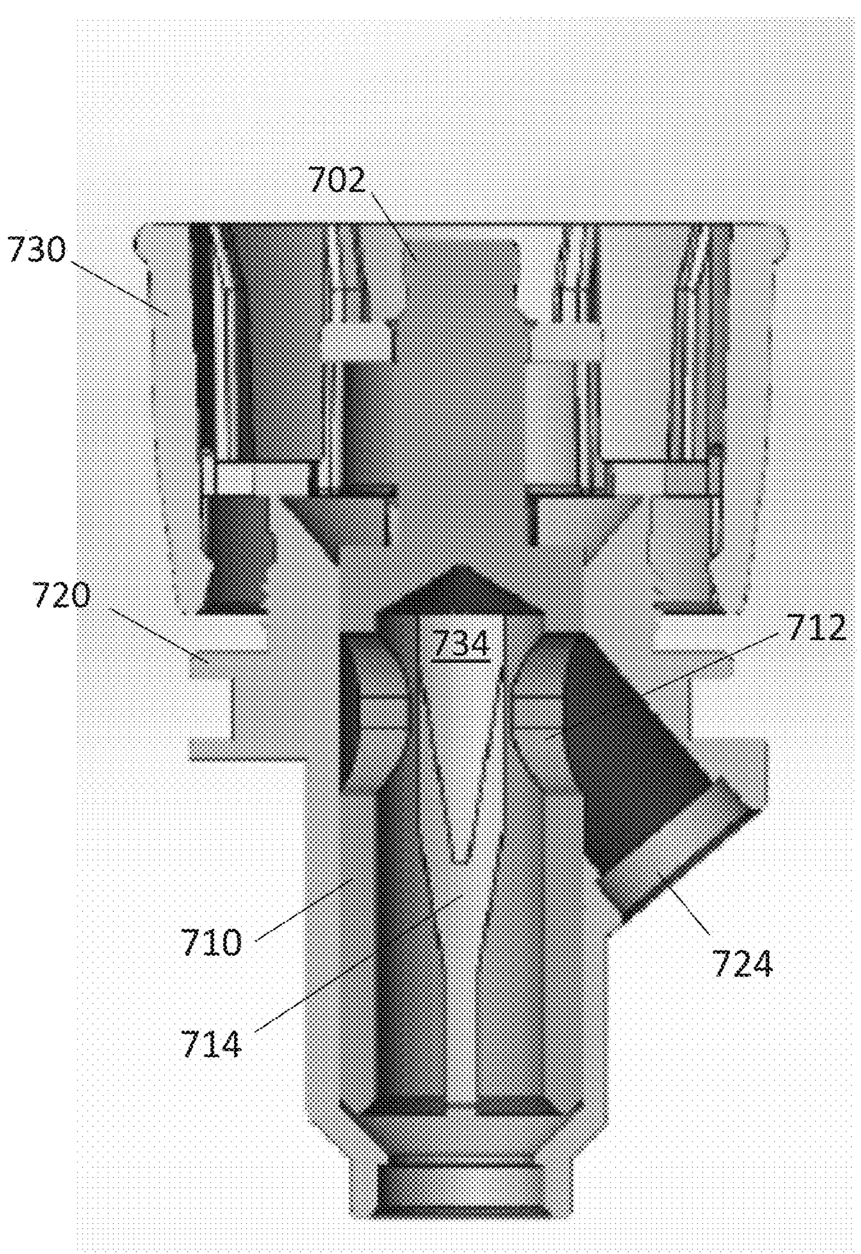
FIG. 7D depicts a cross-section view of an illustrative suction valve assembly, including the suction valve member and valve skirt of FIGS. 7A-7C, in an open position.

As shown in FIG. 7D, when a user presses on the cap 702, the valve member 700 slides downward within the valve well 322 until the inlet opening 712 aligns with the passage 724 allowing for flow into the valve member 700. At the same time, the one or more wedges 734 disengage from the sides of the valve shaft 710, allowing the sides of the valve shaft 710 to relax inward.

The valve member may be manufactured of relatively inexpensive materials suitable for disposal after a single use. The cap, neck, and shaft may be contiguously manufactured from a single piece of polycarbonate plastic; each component may be manufactured from a separate piece of plastic and then attached together. Each of the components of the valve member may, in some implementations, be made of the same or similar materials, with the thickness and dimensions of each piece chosen to provide the necessary resilience and hardness.

In some implementations, the valve shaft may be injection-molded or extruded with one or more of the openings and/or slits not yet present, and then tooling, cutting, or another appropriate technique may be used to remove portions of the shaft in order to form the openings and/or slits. In some implementations, ribs, flanges, wedges, and other smaller features may be cut from the same original piece of material as the surrounding components or may be formed separately (of the same or different material) and then attached as shown.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A suction valve assembly for a medical device, comprising:

a valve body having a cylindrical valve well with internal walls, an inlet channel in fluid communication with the valve well, and an outlet channel in fluid communication with the valve well;

a valve member having a valve shaft, the valve shaft having an inlet opening and positioned within the valve well to slide along the internal walls between a closed position where the inlet opening abuts a portion of the internal walls and an open position where the inlet opening is aligned with the inlet channel of the valve body;

wherein the valve shaft has one or more slits extending through a side surface of the shaft allowing the valve shaft to expand outwards, the valve shaft biased to expand outwards to a diameter greater than an inner diameter defined by the internal walls of the cylindrical valve well; and a valve skirt having one or more wedge members, the valve skirt configured such that, when the valve shaft is in the closed position, each of the one or more wedge members presses against one of the one or more slits in the valve shaft to bias the valve shaft outwards towards the internal walls of the valve well.

2. The suction valve assembly of claim 1, the valve member further comprising a cap accessible from outside the valve body, the cap in mechanical communication with the valve shaft such that actuating the cap slides the valve shaft into the open position.

3. The suction valve assembly of claim 2, wherein valve member further comprises a neck connecting the valve cap to the valve shaft.

4. The suction valve assembly of claim 3, wherein the neck includes a flat portion and a rounded portion shaped to resist rotation of the valve member within the valve body.

5. The suction valve assembly of claim 1, wherein the valve well extends the length of the longest dimension of the valve body between a top face and an opposing bottom face of the valve body.

6. The suction valve assembly of claim 5, wherein the inlet channel is positioned within an internal wall of the valve well.

7. The suction valve assembly of claim 5, wherein the outlet channel is positioned within the bottom face of the valve body.

8. The suction valve assembly of claim 1, wherein the valve shaft has only one slit extending through a side surface of the shaft allowing the valve shaft to expand outwards.

9. The suction valve assembly of claim 1, wherein the valve shaft has two slits extending through side surfaces of the shaft allowing the valve shaft to expand outwards.

10. The suction valve assembly of claim 9, wherein the two slits are on opposite sides of the valve shaft.

11. The suction valve assembly of claim 1, wherein the valve member comprises a plurality of ribs across the one or more slits within the valve shaft.

12. The suction valve assembly of claim 1, wherein the valve member comprises a single piece of uniform material.

13. The suction valve assembly of claim 1, wherein the valve member is made of polycarbonate plastic.

14. A suction valve assembly for use in an endoscope having a lumen configured to extend into a patient's body cavity, the suction valve assembly comprising:

a valve body having a cylindrical valve well with internal walls, an inlet channel in fluid communication with the valve well, and an outlet channel in fluid communication with the valve well;

a valve member having a valve shaft, the valve shaft having an inlet opening and positioned within the valve well to slide along the internal walls between a closed position where the inlet opening abuts a portion of the internal walls and an open position where the inlet opening is aligned with the inlet channel of the valve body;

wherein the valve shaft has one or more slits extending through a side surface of the shaft allowing the valve shaft to expand outwards, the valve shaft biased to expand outwards to a diameter greater than an inner diameter defined by the internal walls of the cylindrical valve well; and a valve skirt having one or more wedge members, the valve skirt configured such that, when the valve shaft is in the closed position, each of the one or more wedge members presses against one of the one or more slits in the valve shaft to bias the valve shaft outwards towards the internal walls of the valve well.

15. The suction valve assembly of claim 14, the valve member further comprising a cap accessible from outside the valve body, the cap in mechanical communication with the valve shaft such that actuating the cap slides the valve shaft into the open position.

16. The suction valve assembly of claim 14, wherein the valve shaft has only one slit extending through a side surface of the shaft allowing the valve shaft to expand outwards.

17. The suction valve assembly of claim 14, wherein the valve shaft has two slits extending through side surfaces of the shaft allowing the valve shaft to expand outwards.

18. An endoscopic surgical device, comprising:

an endoscopic probe;

a suction valve assembly, comprising:

a valve body having a cylindrical valve well with internal walls, an inlet channel in fluid communication with the valve well, and an outlet channel in fluid communication with the valve well, a valve member having a valve shaft, the valve shaft having an inlet opening and positioned within the valve well to slide along the internal walls between a closed position where the inlet opening abuts a portion of the internal walls and an open position where the inlet opening is aligned with the inlet channel of the valve body, wherein the valve shaft has one or more slits extending through a side surface of the shaft allowing the valve shaft to expand outwards, the valve shaft biased to expand outwards to a diameter greater than an inner diameter defined by the internal walls of the cylindrical valve well, and a valve skirt having one or more wedge members, the valve skirt configured such that, when the valve shaft is in the closed position, each of the one or more wedge members presses against one of the one or more slits in the valve shaft to bias the valve shaft outwards towards the internal walls of the valve well; and a source of suction in fluid communication with the inlet passage of the suction valve assembly, such that opening the valve provides suction to the endoscopic probe from the inlet channel, through the valve well, and into the outlet channel.

19. The endoscopic surgical device of claim 18, wherein the valve member further comprises a cap accessible from outside the valve body, the cap in mechanical communication with the valve shaft such that actuating the cap slides the valve shaft into the open position.

20. The endoscopic surgical device of claim 18, wherein the valve shaft has two slits extending through side surfaces of the shaft allowing the valve shaft to expand outwards.

* * * * *